United States Patent
Newton

(10) Patent No.: US 8,071,338 B2
(45) Date of Patent: Dec. 6, 2011

(54) SUPPRESSION OF AMPLIFICATION USING AN OLIGONUCLEOTIDE AND A POLYMERASE SIGNIFICANTLY LACKING 5'-3' NUCLEASE ACTIVITY

(75) Inventor: Nicolas Newton, Oakland, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 413 days.

(21) Appl. No.: 12/186,311

(22) Filed: Aug. 5, 2008

(65) Prior Publication Data

US 2009/0053720 A1 Feb. 26, 2009

Related U.S. Application Data

(60) Provisional application No. 60/964,089, filed on Aug. 8, 2007.

(51) Int. Cl.
*C01P 19/34* (2006.01)
*C07H 21/02* (2006.01)
(52) U.S. Cl. ...................................... 435/91.2
(58) Field of Classification Search ................... None
See application file for complete search history.

(56) References Cited

U.S. PATENT DOCUMENTS 5,849,497 A 12/1998 Steinman
6,534,293 B1 * 3/2003 Barany et al. ................ 435/91.2

FOREIGN PATENT DOCUMENTS

| EP | 0725148 A2 | 8/1996 |
|---|---|---|
| WO | WO 99/61661 A1 | 12/1999 |
| WO | WO 02/086155 A2 | 10/2002 |
| WO | WO 2005/093101 A1 | 10/2005 |
| WO | WO 2006/026828 A1 | 3/2006 |

OTHER PUBLICATIONS

Mulholland (1996) communication provided.*
Wilhelm et al. (2001) Biotechniques May 30 (5): pp. 1052-1056, 1058, 1060 (abstract provided).*
Dominguez, Patrick L. et al.; "Wild-type blocking polymerase chain reaction for detection of single nucleotide minority mutations from clinical specimens"; 2005, *Oncogene*, vol. 24, No. 45, pp. 6830-6834.
Luo, Ji-Dung et al.; "Detection of rare mutant K-ras DNA in a single-tube reaction using peptide nucleic acid as both PCR clamp and sensor probe"; 2006, *Nucleic Acids Research*, vol. 34, No. 2, p. e12.
Oerum, H. et al.; "Single Base Pair Mutation Analysis by PNA-Directed PCR Clamping"; 1993, *Nucleic Acids Research*, vol. 21, No. 23, pp. 5332-5336.
Seyama, T. et al.; "A novel blocker-PCR method for detection of rare mutant alleles in the presence of an excess amount of normal DNA"; 1992, *Nucleic Acids Research*, vol. 20, No. 10, pp. 2493-2496.

* cited by examiner

*Primary Examiner* — Teresa E Strzelecka
*Assistant Examiner* — Suchira Pande
(74) *Attorney, Agent, or Firm* — Kilpatrick Townsend & Stockton LLP

(57) ABSTRACT

Methods and compositions for amplification of a target sequence by suppressing amplification of related sequences are provided.

13 Claims, 6 Drawing Sheets unstabilized probe/ZO5 unstabilized probe ΔZO5 stabilized probe ΔZO5

US 8,071,338 B2

SUPPRESSION OF AMPLIFICATION USING AN OLIGONUCLEOTIDE AND A POLYMERASE SIGNIFICANTLY LACKING 5'-3' NUCLEASE ACTIVITY

CROSS-REFERENCE TO RELATED PATENT APPLICATIONS

The present application claims benefit of priority to U.S. Provisional Patent Application No. 60/964,089, filed Aug. 8, 2007, which is incorporated by reference in its entirety.

BACKGROUND OF THE INVENTION

Numerous examples of the need for quick and reliable nucleic acid classification/identification exist, especially in fields such as medicine. For example, many diseases including cancer are the result of rare mutations. Detecting these mutations can assist in determinations of diagnosis and prognosis.

Additionally, quick and reliable means of genotyping can be helpful in determining allele composition within and amongst individuals. For example, reliable classification of particular alleles in an individual can help in genetic counseling in humans and can even help in planning prophylactic treatment in instances when specific alleles are detected. Identification of particular alleles is also extremely useful in performing marker assisted selection, e.g., crop or animal breeding programs, identifying or genotyping pathogens and other organisms.

BRIEF SUMMARY OF THE INVENTION

This invention provides methods of detecting a target sequence in a polynucleotide in a biological sample, wherein the sample may also, or alternatively, contain a second polynucleotide comprising a second sequence, wherein the second sequence differs from the target sequence by at least one nucleotide. In some embodiments, the methods comprise,
i. contacting the sample with a blocker oligonucleotide under conditions to allow for hybridization of the blocker oligonucleotide to the second sequence or the target sequence, if present,
ii. contacting the sample in the presence of the hybridized blocker oligonucleotide with at least one primer and a polymerase significantly lacking 5'-3' nuclease activity under conditions such that template-dependent extension of the primer occurs, wherein the primer hybridizes to either of the polynucleotides, if present, upstream of the blocker oligonucleotide-hybridizing sequence;
wherein the blocker oligonucleotide hybridizes to the second sequence sufficiently to impair amplification of the second sequence by the polymerase, and further wherein hybridization of the oligonucleotide to the target sequence does not significantly impair amplification of the target sequence by the polymerase significantly lacking 5'-3' nuclease activity.

The present invention also provides reaction mixtures. In some embodiments, the reaction mixtures comprise: a polymerase significantly lacking 5'-3' nuclease activity; a polynucleotide comprising a target sequence; a polynucleotide comprising a second sequence, wherein the second sequence differs from the target sequence by at least one nucleotide; and a blocker oligonucleotide that hybridizes to the second sequence and the target sequence; wherein the blocker oligonucleotide hybridizes to the second sequence sufficiently to impair amplification of the second sequence by the polymerase under conditions suitable for amplification in the absence of the blocker oligonucleotide, but hybridization of the oligonucleotide to the target sequence does not significantly impair amplification of the target sequence by the polymerase significantly lacking 5'-3' nuclease activity.

The present invention also provides kits. In some embodiments, the kits comprise a polymerase significantly lacking 5'-3' nuclease activity; a polynucleotide comprising a target sequence; a polynucleotide comprising a second sequence, wherein the second sequence differs from the target sequence by at least one nucleotide; and a blocker oligonucleotide that hybridizes to the second sequence and the target sequence, wherein the blocker oligonucleotide hybridizes to the second sequence sufficiently to impair amplification of the second sequence by the polymerase under conditions suitable for amplification in the absence of the blocker oligonucleotide, but hybridization of the oligonucleotide to the target sequence does not significantly impair amplification of the target sequence by the polymerase significantly lacking 5'-3' nuclease activity.

In some embodiments of the methods, kits or mixtures described herein, the blocker oligonucleotide does not comprise an intercalating nucleotide.

In some embodiments of the methods, kits or mixtures described herein, the blocker oligonucleotide hybridizes to the second sequence sufficiently to impair amplification of the second sequence by the polymerase significantly lacking 5'-3' nuclease activity but does not hybridize sufficiently to impair amplification of a polymerase having 5'-3' nuclease activity.

In some embodiments of the methods, kits or mixtures described herein, the target sequence is between 5-100 nucleotides long.

In some embodiments of the methods, kits or mixtures described herein, the sample comprises the target sequence and the second sequence. In some embodiments of the methods, kits or mixtures described herein, the second sequence are present in the sample at a concentration at least ten-fold higher than the concentration of target sequence. In some embodiments of the methods, kits or mixtures described herein, the concentration of the target sequence and the second sequence is in a ratio of about 1:1.

In some embodiments of the methods, kits or mixtures described herein, the polynucleotides are genomic DNA. In some embodiments, the polynucleotides are RNA.

In some embodiments of the methods, kits or mixtures described herein, the blocker oligonucleotide is detectably-labeled. In some embodiments of the methods, kits or mixtures described herein, the detectably-labeled blocker oligonucleotide is detected in real-time, thereby detecting amplification of the target sequence.

In some embodiments of the methods, kits or mixtures described herein, there is a single nucleotide difference between the second and target sequences and the blocker oligonucleotide is fully complementary to the target sequence except for at the position of the single nucleotide. In some embodiments of the methods, kits or mixtures described herein, there are 2-6 nucleotide differences between the second and target sequences and the blocker oligonucleotide is fully complementary to the target sequence except for at the positions of the 2-6 nucleotides.

In some embodiments of the methods, kits or mixtures described herein, the difference between: the melting temperature of the blocker oligonucleotide and the second sequence; and the melting temperature of the blocker oligonucleotide and the target sequence, is at least 5° C. as measured in 2.5% glycerol, 50 mM Tricine pH 8.3, 45 mM potassium acetate. In some embodiments of the methods, kits or mixtures described herein, the $T_m$ of the blocker oligonucleotide for the second sequence is no more than 20° C. higher than the Tm of the blocker oligonucleotide for the target sequence as measured in 2.5% glycerol, 50 mM Tricine pH 8.3, 45 mM potassium acetate In some embodiments of the methods, kits or mixtures described herein, the blocker oligonucleotide comprises at least one non-natural non-intercalating nucleotide, wherein the non-natural nucleotide increases the melting temperature of the blocker oligonucleotide compared to a control oligonucleotide that is otherwise identical to the blocker oligonucleotide except has a natural nucleotide in the place of the non-natural nucleotide.

In some embodiments of the methods, kits or mixtures described herein, the blocker oligonucleotide comprises at least one non-nucleotide moiety, wherein the non-nucleotide moiety increases the melting temperature of the blocker oligonucleotide compared to a control oligonucleotide that is otherwise identical to the blocker oligonucleotide except lacks the non-nucleotide moiety. In some embodiments of the methods, kits or mixtures described herein, the non-nucleotide moiety binds a minor groove of DNA.

In some embodiments of the methods, kits or mixtures described herein, the blocker oligonucleotide hybridizes to the second sequence with a melting temperature of at least 70° C. as measured in 2.5% glycerol, 50 mM Tricine pH 8.3, 45 mM potassium acetate.

DEFINITIONS

As used in this specification and the appended claims, the singular forms "a," "an," and "the" include plural referents unless the context clearly dictates otherwise. Thus, for example, reference to "an oligonucleotide" includes a plurality of oligonucleotides; reference to "a probe" includes mixtures of such probes, and the like.

As used herein, a "biological sample" refers to any substance containing or presumed to contain nucleic acid (e.g., from a bacteria, virus, tissue biopsy etc.). The sample can be obtained by any means known to those of skill in the art. Such sample can be an amount of tissue or fluid, or a purified fraction thereof, isolated from an individual or individuals, including, but not limited to, for example, skin, plasma, serum, whole blood, spinal fluid, saliva, peritoneal fluid, lymphatic fluid, aqueous or vitreous humor, synovial fluid, urine, tears, blood cells, blood products, semen, seminal fluid, vaginal fluids, pulmonary effusion, serosal fluid, organs, bronchio-alveolar lavage, tumors, paraffin embedded tissues, etc. Samples also can include constituents and components of in vitro cell cultures, including, but not limited to, conditioned medium resulting from the growth of cells in the cell culture medium, recombinant cells, cell components, etc. A nucleic acid can be obtained from a biological sample by procedures well known in the art.

A "blocker oligonucleotide" as used herein refers to an oligonucleotide that:

(1) forms a duplex with a target sequence at a sufficiently low melting temperature to allow for a polymerase significantly lacking 5'-3' nuclease activity to displace the blocker oligonucleotide and to replicate the target sequence; and (2) forms a duplex with a second sequence that is a variant of the target sequence at a sufficiently high melting temperature to impair a polymerase significantly lacking 5'-3' nuclease activity from replicating the target sequence.
The blocker oligonucleotide can, but need not, include a modification at the 3' end to prevent 3' extension of the blocker oligonucleotide by a polymerase.

A "target sequence" refers to a polynucleotide sequence to be detected in a biological sample and is the region (a subsequence or sequence) of a nucleic acid that is fully or partially complementary to the hybridizing region of a blocker oligonucleotide. The "target sequence" can be of any length at least 5 nucleotides long. The target sequence can be a portion of a larger gene sequence or other sequence to be detected.

The phrase "impair amplification" refers to eliminating, inhibiting or measurably reducing amplification (i.e., template-dependent replication) of a sequence. As described herein, by selecting a blocker oligonucleotide that has a higher melting temperature for a target variant than for the target, it is possible to impair amplification of the target variant (e.g., wherein amplification is less than 50%, 25%, 10%, 5%, 1%, 0.1%, 0.001%, 00001% compared to control reaction lacking the blocker oligonucleotide), thereby allowing for improved amplification and detection of the target sequence.

The terms "nucleic acid" and "polynucleotide" are used interchangeably, and refer to a polymer of monomers of ribose nucleic acids (RNA) or deoxyribose nucleic acids (DNA) polymer or analogs thereof. This includes polymers of nucleotides such as RNA and DNA, as well as modified forms thereof, peptide nucleic acids (PNAs), locked nucleic acids (LNA), and the like. In certain applications, the nucleic acid can be a polymer that includes multiple monomer types, e.g., both RNA and DNA subunits. A nucleic acid can be or include, e.g., a chromosome or chromosomal segment, a vector (e.g., an expression vector), an expression cassette, a naked DNA or RNA polymer, an amplicon, an oligonucleotide, a primer, a probe, etc. A nucleic acid can be e.g., single-stranded or double-stranded, or DNA:RNA hybrids, DNA and RNA chimeric structures. There is no intended distinction in length between the term "nucleic acid," "polynucleotide," and "oligonucleotide," and the terms can be used interchangeably herein unless the context clearly dictates otherwise. Such terms refer only to the primary structure of the molecule.

"Extension of a primer" refers to the ability of a nucleotide incorporating biocatalyst, such as a polymerase, to add nucleotides to the 3' terminus of a primer in a template-specific manner. Extension does not only refer to the first nucleotide added to the 3' terminus of a primer, but also includes any further extension of a polynucleotide formed by the extended primer.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10): 1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphosphoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook. Nucleic acids containing one or more carbocyclic sugars are also included within the definition of nucleic acids (Jenkins et al. (1995) *Chem. Soc. Rev.* pp 169-176). Several nucleic acid analogs are also described in, e.g., Rawls, C & E News Jun. 2, 1997 page 35. These modifications of the ribose-phosphate backbone may be done to facilitate the addition of additional moieties such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640. To further illustrate, certain bases used in nucleotides that act as melting temperature (Tm) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 7-deazaadenine, 2-methyladenine, 2-methylguanine, 3-methylcytosine, 5-methylcytosine, N6-methyladenine, 7-methylguanine, 7-deazaguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine, and the like.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDNES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003.

It is not intended that the present invention be limited by the source of a nucleic acid, polynucleotide or oligonucleotide. Such nucleic acid can be from a human or non-human mammal, or any other organism (e.g., plant, amphibian, bacteria, virus, mycoplasm, etc.), tissue, or cell line, or derived from any recombinant source, synthesized in vitro or by chemical synthesis. Again, the nucleic acid can be DNA, RNA, cDNA, DNA-RNA, locked nucleic acid (LNA), peptide nucleic acid (PNA), a hybrid or any mixture of the above. The nucleic acid can exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, mycoplasms, and the like.

"Polymerase chain reaction extension conditions" refer to conditions under which primers that hybridize to a template nucleic acid are extended by a polymerase during a polymerase chain reaction (PCR) annealing step. Those of skill in the art will appreciate that such conditions can vary, and are generally influenced by ionic strength and temperature. Various PCR annealing conditions are described in, e.g., *PCR Strategies* (M. A. Innis, D. H. Gelfand, and J. J. Sninsky eds., 1995, Academic Press, San Diego, Calif.) at Chapter 14; *PCR Protocols: A Guide to Methods and Applications* (M. A. Innis, D. H. Gelfand, J. J. Sninsky, and T. J. White eds., Academic Press, NY, 1990).

A nucleic acid is "complementary" in relation to another nucleic acid when at least a nucleic acid segment (i.e., at least two contiguous bases) can combine in an antiparallel association or hybridize with at least a subsequence of other nucleic acid to form a duplex. The antiparallel association can be intramolecular, e.g., in the form of a hairpin loop within a nucleic acid, or intermolecular, such as when two or more single-stranded nucleic acids hybridize with one another. In the context of the present invention, for an oligonucleotide that is "fully complementary" to particular sequence, each base of the oligonucleotide is complementary to the corresponding bases in the particular sequence in an anti-parallel manner. Certain bases not commonly found in natural nucleic acids may be included in the nucleic acids of the present invention and include, for example, inosine, 7-deazaguanine and those discussed above. In some embodiments, complementarity is not perfect (i.e., nucleic acids can be "partially complementary" rather than "fully complementary"). Stable duplexes, for example, may contain mismatched base pairs or unmatched bases.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. Such conditions typically include the presence of one or more deoxyribonucleoside triphosphates and the nucleotide incorporating biocatalyst, in a suitable buffer ("buffer" includes substituents which are cofactors, or which affect pH, ionic strength, etc.), and at a suitable temperature. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 6 to about 100 nucleotides in length. Short primer nucleic acids generally require lower temperatures to form sufficiently stable hybrid complexes with template nucleic acids. A primer nucleic acid that is at least partially complementary to a subsequence of a template nucleic acid is typically sufficient to hybridize with the template for extension to occur. The design of suitable primers for, e.g., the amplification of a given target sequence is well known in the art and described in the literature cited herein. A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or otherwise known in the art. One of skill in the art will recognize that, in certain embodiments, primer nucleic acids can also be used as probe nucleic acids.

As used herein, the term "probe" refers to an oligonucleotide (or other nucleic acid sequence) which can form a duplex structure with a region of a target nucleic acid (or amplicon derived from such target nucleic acid), due to partial or complete complementarity of at least one sequence in the probe with a sequence in the target nucleic acid under suitable conditions. As discussed herein, the probe can be labeled or unlabeled. The 3'-terminus of the probe optionally can be designed to prohibit incorporation of the probe into a primer extension product. This can be achieved by using non-complementary bases or by adding a chemical moiety such as biotin or a phosphate group to the 3'-hydroxyl group of the last nucleotide, which can, depending upon the selected moiety, serve a dual purpose by also acting as a label for subsequent detection or capture of the nucleic acid attached to the label. Prohibiting extension can also be achieved by removing the 3'-OH or by using a nucleotide that lacks a 3'-OH such as a dideoxynucleotide, or by adding a bulky group that blocks extension by steric hindrance. As discussed further herein, the blocker oligonucleotides of the invention can, but do not necessarily, function as probes.

The term "hybridizing region" refers to that region of a nucleic acid that is exactly or substantially complementary to, and therefore hybridizes to, a polynucleotide and is at least 5 contiguous nucleotides in length. Although the hybridizing region generally refers to a region of a nucleic acid that hybridizes to the entire blocker oligonucleotide, the blocker nucleotide can in some embodiments also include additional nucleotide sequences that do not hybridize but instead function, for example, as a linker, tag, a flap, or the like. In some embodiments, the hybridizing region of the blocker oligonucleotide is completely complementary to the target sequence. However, as described herein, complete complementarity is not necessary (for example, there is generally at least one mismatch resulting in only partial complementarity between a blocker oligonucleotide and the target sequence).

As defined herein, "5' to 3' nuclease activity" refers to an activity of a template-specific nucleic acid polymerase that includes a 5' to 3'-nuclease activity (traditionally associated with some DNA polymerases whereby nucleotides are removed from the 5' end of an oligonucleotide in a sequential manner, e.g., *E. coli* DNA polymerase I has this activity whereas the Klenow fragment does not (additional polymerases are discussed in the paragraph below).

A polymerase that "significantly lacks 5'-3'nuclease activity" refers to a polymerase that has 50% (e.g., <25%, <20, <15%, <10%) or less nuclease activity than Taq DNA polymerase. Methods of measuring 5'-3' nuclease activity and conditions for measurement are well known in the art. See, e.g., U.S. Pat. No. 5,466,591. Examples DNA polymerases substantially lacking 5' to 3' nuclease activity include, e.g., any DNA polymerase having undetectable 5' to 3' nuclease activity under typical primer extension conditions for that polymerase. For example, polymerases lacking or having a mutated 5'-3' nuclease domain; the Klenow fragment of *E. coli* DNA polymerase I; a *Thermus aquaticus* DNA polymerase (Taq) lacking the N-terminal 235 amino acids (e.g., as described in U.S. Pat. No. 5,616,494 or as commonly referred to in the art as the "Stoffel fragment"). Other examples include a thermostable DNA polymerase having sufficient deletions (e.g., N-terminal deletions), mutations, or modifications so as to eliminate or inactivate the domain responsible for 5' to 3' nuclease activity. See, e.g., U.S. Pat. No. 5,795,762. Exemplary DNA polymerases include those from *Thermus thermophilus, Thermus caldophilus, Thermus* sp. ZO5 (see, e.g., U.S. Pat. No. 5,674,738), *Thermus aquaticus, Thermus flavus, Thermus filiformis, Thermus* sp. sps17, *Deinococcus radiodurans,* Hot Spring family B/clone 7, *Bacillus stearothermophilus, Bacillus caldotenax, Escherchia coli, Thermotoga maritima, Thermotoga neapolitana, Thermosipho africanus*. The full nucleic acid and amino acid sequence for numerous thermostable DNA polymerases are available. The sequences each of *Thermus aquaticus* (Taq), *Thermus thermophilus* (Tth), *Thermus* species Z05, *Thermus* species sps17, *Thermotoga maritima* (Tma), and *Thermosipho africanus* (Taf) polymerase have been published in PCT International Patent Publication No. WO 92/06200, which is incorporated herein by reference. The sequence for the DNA polymerase from *Thermus flavus* has been published in Akhmetzjanov and Vakhitov (*Nucleic Acids Research* 20:5839, 1992), which is incorporated herein by reference. The sequence of the thermostable DNA polymerase from *Thermus caldophilus* is found in EMBL/GenBank Accession No. U62584. The sequence of the thermostable DNA polymerase from *Thermus filiformis* can be recovered from ATCC Deposit No. 42380 using, e.g., the methods provided in U.S. Pat. No. 4,889,818, as well as the sequence information provided therein. The sequence of the *Thermotoga neapolitana* DNA polymerase is from GeneSeq Patent Data Base Accession No. R98144 and PCT WO 97/09451, each incorporated herein by reference. The sequence of the thermostable DNA polymerase from *Bacillus caldotenax* is described in, e.g., Uemori et al. (*J Biochem* (*Tokyo*) 113(3):401-410, 1993; see also, Swiss-Prot database Accession No. Q04957 and GenBank Accession Nos. D12982 and BAA02361), which are each incorporated by reference. The sequence for the DNA polymerase from *Bacillus stearothermophilus* has been published in U.S. Pat. No. 6,066,483, which is incorporated herein by reference. Examples of unmodified forms of DNA polymerases that can be modified to remove or mutate the 5'-3' nuclease domain include, e.g., U.S. Pat. Nos. 6,228,628;

6,346,379; 7,030,220; 6,881,559; 6,794,177; 6,468,775; and U.S. Pat. Appl. Nos. 20040005599; 20020012970; 20060078928; and 20040115639, which are each incorporated by reference. As explained in U.S. Pat. No. 5,795,762, a site-directed mutation of G to A in the second position of the codon for Gly at residue 46 in the Taq DNA polymerase amino acid sequence (i.e. mutation of G(137) to A in the DNA sequence has been found to result in an approximately 1000-fold reduction of 5' to 3' nuclease activity with no apparent change in polymerase activity, processivity or extension rate. This site-directed mutation of the Taq DNA polymerase nucleotide sequence results in an amino acid change of Gly (46) to Asp. Glycine 46 of Taq DNA polymerase is conserved in *Thermus* species sps17 DNA polymerase, but is located at residue 43, and the same Gly to Asp mutation has a similar effect on the 5' to 3' nuclease activity of Tsps17 DNA polymerase. Such a mutation of the conserved Gly of Tth (Gly 46), TZ05 (Gly 46), Tma (Gly 37) and Taf (Gly 37) DNA polymerases to Asp also has a similar attenuating effect on the 5' to 3' nuclease activities of those polymerases.

As used herein, the term "$T_m$" refers to the "melting temperature." The melting temperature is the temperature at which one half of a population of double-stranded polynucleotides or nucleobase oligomers (e.g., hybridization complexes), in homoduplexes or heteroduplexes (i.e., duplexes that are completely or partially complementary), become dissociated into single strands (under defined ionic strength, pH and nucleic acid concentration). The prediction of a $T_m$ of a duplex polynucleotide takes into account the base sequence as well as other factors including structural and sequence characteristics and nature of the oligomeric linkages. Methods for predicting and experimentally determining $T_m$ are known in the art.

For example, a $T_m$ is traditionally determined by a melting curve, wherein a duplex nucleic acid molecule is heated in a controlled temperature program, and the state of association/dissociation of the two single strands in the duplex is monitored and plotted until reaching a temperature where the two strands are completely dissociated. The $T_m$ is determined from this melting curve. Alternatively, a $T_m$ can be determined by an annealing curve, wherein a duplex nucleic acid molecule is heated to a temperature where the two strands are completely dissociated. The temperature is then lowered in a controlled temperature program, and the state of association/dissociation of the two single strands in the duplex is monitored and plotted until reaching a temperature where the two strands are completely annealed. The $T_m$ is then determined from this annealing curve.

DETAILED DESCRIPTION

I. Introduction

Figure 1:
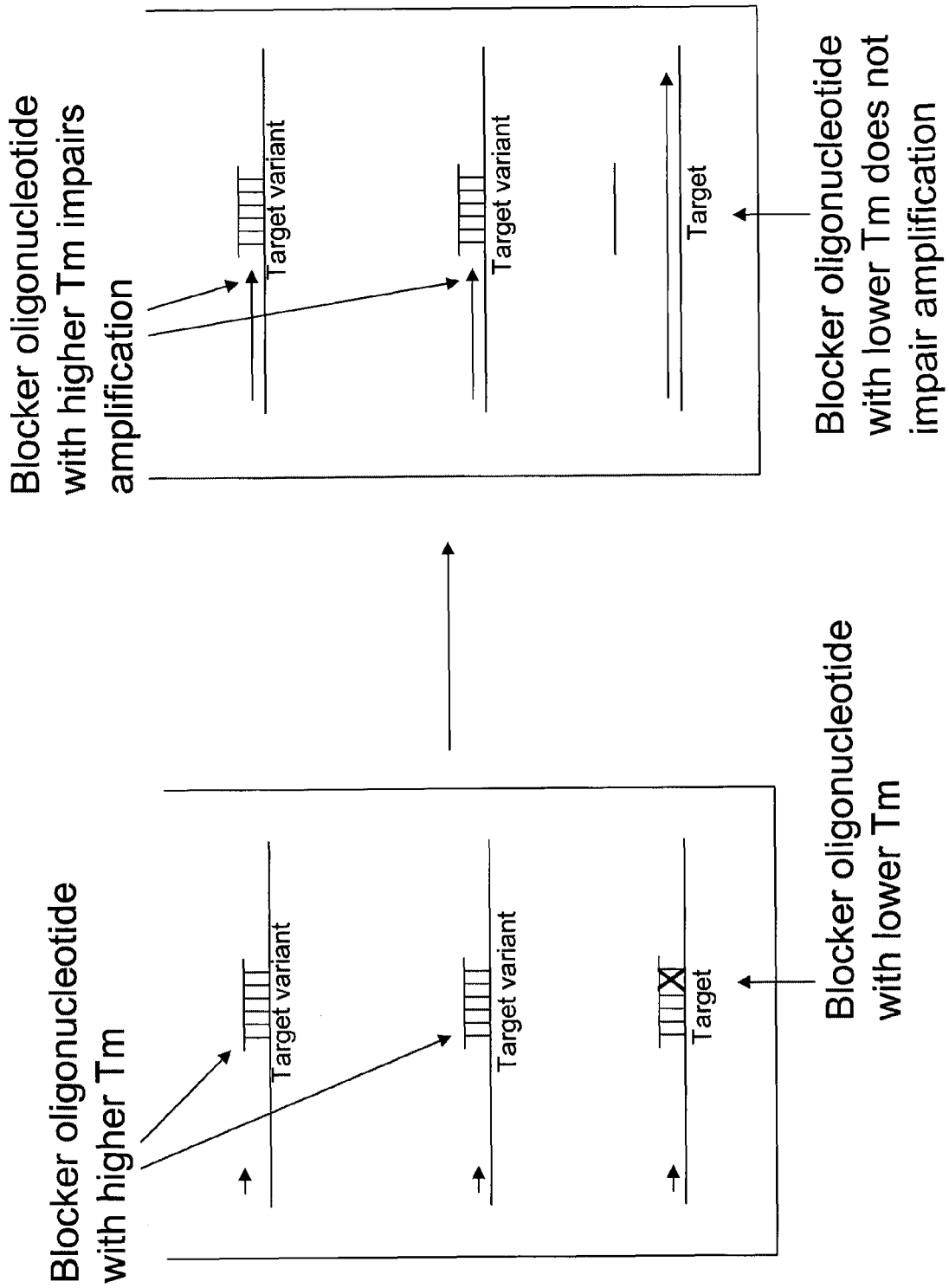
FIG. 1 illustrates an example of suppression of amplification of related sequences while allowing for amplification of a target sequence. The sample shown contains one copy of a target sequence (at bottom) and two copies of a related sequence (two top horizontal lines). The left portion of the figure illustrates hybridization of the blocker oligonucleotide to the sequences. In this example, there is a mismatch in the region of the blocker oligonucleotide and the target sequence, whereas there is no mismatch for the top related sequences, thus resulting in a higher Tm for the related sequences compared to the Tm for the target sequence. The right portion of the figure illustrates how the higher Tm for the related sequences results in impaired (in this case blocked) amplification of the related sequences by the polymerase, whereas amplification is not impaired for the target sequence. While the Figure displays two copies of the target variant and one copy of the target, it will be appreciated that the invention is also useful where there are different ratios of target and variant, including, e.g., 1:10, 1:100, 1:1000, 1:10000, etc.

The present invention is based in part on the surprising finding that an oligonucleotide forming a duplex with a polynucleotide at a sufficiently high melting temperature can impair replication and template amplification by a polymerase that significantly lacks 5'-3' activity, but optionally does not impair replication and template amplification by a polymerase that has 5'-3' nuclease activity. It has been found that this phenomenon can be applied to detection of target sequences in the presence of target variant sequences (also sometimes referred to herein as a "second sequence") by designing the oligonucleotide (designated a "blocker oligonucleotide") such that the blocker oligonucleotide forms a duplex with the variant at a sufficiently high melting temperature to impair amplification of the variant whereas the melting temperature of the duplex formed by the blocker oligonucleotide and the target is lower, and thus the blocker oligonucleotide does not significantly impair amplification of the target. Thus, in some embodiments, the methods of the invention are useful for detecting a particular target sequence in a mixture of highly related sequences.

In a simple example not intended to limit the scope of the invention, an oligonucleotide is designed such that the oligonucleotide is fully complementary to a target variant sequence, and thus forms a duplex with a $T_m$ that impairs the polymerase lacking 5'-3' nuclease activity from significantly amplifying the target variant. In this example, the target has a single nucleotide difference from the variant and thus the oligonucleotide also forms a duplex with the target, but with at least one mismatched base pair. The mismatched base pair results in a reduced $T_m$ of the duplex formed by the blocker oligonucleotide with the target compared to the duplex formed with the variant sequence, and the reduction in Tm is sufficient to allow the polymerase to amplify the target sequence and not significantly impair the polymerase from replicating the template to which the blocker oligonucleotide hybridizes.

The present invention therefore provides for methods of detecting target sequences even in the presence of other different but highly related sequences, and even if the related sequences are in significantly higher quantity than the target sequence. Accordingly, the methods of the invention are useful for numerous applications including, for example, detection of mutations indicative of cancer or other disease.

II. Overview of the Methods of the Invention

The present invention takes advantage of differences in hybridization affinity of a blocker oligonucleotide for a target sequence and a target variant sequence, wherein the blocker oligonucleotide forms a duplex with a higher $T_m$ (i.e., a higher affinity) for one or more target variant sequences compared to the $T_m$ for the target sequence. In some embodiments, for example, the lower $T_m$ between the blocker oligonucleotide and the target sequence is the result of at least one mismatch in the hybridizing region. For example, the blocker oligonucleotide can be designed to be fully complementary to the target variant sequence, but only partially complementary to the target sequence. Mismatches can be the result of, for example, insertions, deletions, or nucleotide substitutions, thereby resulting in differences between the target and target variant sequences.

In some embodiments, a sample that may have a nucleic acid with the target sequence and/or a nucleic acid with a target variant is contacted with a blocker oligonucleotide under conditions to allow for hybridization of the blocker oligonucleotide to the target sequence (if present) and the target variant sequence (if present). A primer extension reaction is then performed where a primer is hybridized to the nucleic acids at a region upstream of the region of the nucleic acid where the blocker oligonucleotide hybridizes. As used herein, a "primer extension reaction" refers to any reaction that results in extension of one or more primers, and thus the term encompasses, for example, polymerase chain reactions. The position on the nucleic acid at which the primer hybridizes is determined such that extension of the primer is blocked by the blocker oligonucleotide if the blocker oligonucleotide hybridizes to the nucleic acid with sufficient affinity (i.e., the blocker oligonucleotide has a sufficiently high $T_m$). The primer extension reaction is performed with a polymerase that significantly lacks 5'-3' nuclease activity. As discussed herein, the inventors have found that polymerases significantly lacking 5'-3' nuclease activity cannot displace the blocker oligonucleotide if the blocker oligonucleotide hybridizes with a sufficiently high affinity, whereas in some embodiments a polymerase having 5'-3' nuclease activity can displace the blocker (thereby acting as a useful control, if desired). Thus the primer extension reaction is generally only completed (i.e., a full extension of the primer is achieved) where the nucleic acid contains the target sequence (i.e., a sequence to which the blocker oligonucleotide does not have sufficient affinity) when a polymerase significantly lacking 5'-3' nuclease activity is used.

FIG. 1 illustrates the above-described method. The left side of FIG. 1 represents a sample in a tube in which there are two copies of a nucleic acid comprising a target variant and one copy of a nucleic acid comprising the target sequence. The blocker oligonucleotide is contacted with the nucleic acids and hybridizes to the target or target variant sequences. Because the target sequence comprises at least one nucleotide difference from the target variant, the blocker oligonucleotide is not fully complementary with the target sequence (displayed in FIG. 1 with an "X"). Thus, while the blocker oligonucleotide hybridizes to the target sequence, it does so with a lower $T_m$ than the $T_m$ of the blocker oligonucleotide and the target variant.

The right side of FIG. 1 illustrates the resulting primer extension reaction. The primer is represented by a small arrow that hybridizes towards the left of each nucleic acid. When the primer is extended by a polymerase significantly lacking 5'-3' nuclease activity on nucleic acids comprising target variants, the hybridization of the blocker oligonucleotide impairs (i.e., inhibits at least some, and typically most, or nearly all of) the extension across the target variant sequences, and thus results in incomplete extension. In contrast, because the blocker oligonucleotide hybridizes with lower affinity (i.e., lower $T_m$) to the target sequence, the polymerase is able to extend the primer across the target sequence (presumably by displacing the blocker oligonucleotide).

The target and the target variant sequence will differ by at least one nucleotide (e.g., an insertion, deletion or changed nucleotide) in the hybridizing region, i.e., the region at which the blocker oligonucleotide hybridizes to the sequences. Generally, the target and target variant will be similar enough such that the blocker oligonucleotide can hybridize to the target and target variant under the same conditions, e.g., the conditions of a primer extension reaction including but not limited to an amplification reaction such as a PCR or other amplification reaction. Thus, in some embodiments, the target and target variant differ in the hybridizing region by 1, 2, 3, 4, 5, 6, 7, 8, 9, or more nucleotides, e.g., 1-5, 1-4, 1-3, 1-2, 2-3, 2-4, 2-5, 1-20, 2-20 nucleotides. In some embodiments, the target sequence is less than 100% identical than the target variant sequence, but is more than, e.g., 80%, 85%, 90%, 95%, 97%, 98%, or 99% identical. In numerous embodiments, the difference(s) between the target and target variant sequences occur in internal portions of the sequences rather than as the terminal 5' or 3' nucleotide.

The target sequence can be of any length. In some embodiments, the target nucleotide is at least 5 nucleotides in length, e.g., at least 10, 15, 20 or more nucleotides, e.g., 5-200, 5-100, 10-200, 10-100, 10-50, 15-50, 20-80 nucleotides, etc.

While this disclosure generally discusses the invention as if there is one target and one target variant, it will be appreciated that in some embodiments there are multiple different target sequences and/or target variant sequences within a sample. In some embodiments, there are or are possibly more than one different target variant sequence in the sample with the target sequence. Thus, for example, a sample can contain a target sequence, one target variant with one nucleotide difference from the target sequence and a second target variant with a different nucleotide difference from the target sequence.

In some embodiments, "multiplex" reactions can be performed where at least two different target sequences are detected. These embodiments generally, but not always, involve the use of two or more (e.g., 2, 3, 4, 5, etc., depending on the number of targets to be detected) different blocker oligonucleotides, wherein each blocker oligonucleotide impairs extension of variants of different target sequences.

The distance between the region of the nucleic acid where the primer hybridizes and the blocker oligonucleotide hybridizes can vary so long as the distance is not so far that the extension reaction is completed before reaching the region where the blocker oligonucleotide hybridizes. In some embodiments, the distance between the nucleotide at which the 3' most portion of the primer hybridizes and the 5' most portion of the blocker nucleotide is between about 5-1000 nucleotides, e.g., 10-100 nucleotides, but can be as small as zero (adjacent).

Primers used for primer extension can be identical between those that hybridize to nucleic acids having a target variant and those having the target sequence, but the primers can also be different. For example, where it is desired to detect a rare somatic mutation in an organism, the genome of the organism will generally be identical except for the change at the mutation site. Thus, the target sequence will comprise the mutation site, and an identical primer can be used because the region upstream of the mutation site, whether or not the mutation site is mutated, will have the same sequence. Nevertheless, while possibly more rare, there are situations that can be envisioned in which the primers used for the extension reactions of the target and target variant nucleic acids are different and therefore such embodiments are not precluded from the invention.

The extension products can be detected, and the aborted target variant extension products can be distinguished from the target extension products, by numerous methods. In some embodiments, polymerase chain reaction (PCR) or other type of nucleic acid amplification is used. For PCR reactions, two primers are typically used. As used in the methods of the invention, one PCR primer is the primer discussed with reference to the "primer extension" reactions above, and the second primer (e.g., a reverse primer) is designed to hybridize to a complement of a sequence on the nucleic acid that is downstream of the blocker oligonucleotide. As used in the methods of the inventions, PCR is useful in that exponential amplification occurs only for those reactions in which the polymerase is capable of displacing the blocker oligonucleotide (i.e., those involving the target sequence). A number of thermostable polymerases significantly lacking 5'-3' nuclease activity are known and described herein. The methods of the invention find particular use in asymmetric PCR reactions, i.e., PCR reactions in which one primer is in limiting concentration compared to other primers in the reaction. Generally, the primer (the reverse primer in the above example) that generates the strand to which the blocker oligonucleotide hybridizes is the primer in limiting concentration.

Regardless of the type of primer extension reaction performed, numerous different types of methods can be used to detect the extension products. In some embodiments, a probe (e.g., a detectably-labeled probe) is designed to hybridize to a region of the extension product corresponding to the target sequence or a sequence further downstream from the target sequence on the nucleic acid, or a complement of such sequences. Such a probe would only, or primarily, detect extension products involving nucleic acids comprising the target sequence as extension products from nucleic acids comprising target variants would be impaired and thus would not generally include the target sequence, the target variant sequence, or downstream sequences.

For example, in some embodiments, detectably labeled "real-time" probes are used and function as a blocker oligonucleotide. Such probes can include, but are not limited to, Taqman® probes and molecular beacons. In some embodiments, detectably labeled "real-time" probes (also functioning as blocker oligonucleotides) as used in real-time amplification reactions such as real-time PCR reactions. Cycle threshold (Ct) values are frequently used to monitor target quantities in real-time amplifications. In some embodiments, there is a difference of at least 5, 10, 15 or more Cts between a target and a target variant as determined in a real-time amplification reaction in the presence of equal amounts of target and target variant sequences.

In some embodiments, mass-based detection methods can be used to detect the extension products. As the extension products from nucleic acids comprising the target sequence will generally be significantly longer than those generated from nucleic acids comprising target variant sequences, any method that detects differences in nucleic acid length or mass can be used. For example, various mass spectrometry methods can be used to detect, distinguish, and quantify extension products.

In some embodiments, melting temperature analysis is used to detect the extension products. For example, in some embodiments, the blocker oligonucleotide is labeled and a melting curve analysis is performed to quantify the amount of template to which the labeled oligonucleotide hybridizes.

III. Oligonucleotides that Block Extension of Polymerases with Impaired 5'-3' Nuclease Activity Blocker oligonucleotides of the present invention are designed to hybridize to a target sequence variant with a higher melting temperature (Tm) than the blocker hybridizes to the target sequence itself. The blocker oligonucleotide need not be fully complementary to the target variant so long as the blocker oligonucleotide hybridizes to the target variant with a sufficiently high $T_m$ to impair, under designated conditions, a polymerase from replicating the portion of a template to which the blocker oligonucleotide hybridizes. In some embodiments, the blocker oligonucleotide is fully complementary to a target variant but forms at least one mismatch (e.g., 1, 2, 3, 4, 5, 6, 7, 1-3, 1-4, 2-6 mismatches, etc.) when hybridizing with the target sequence, thereby resulting in a lower Tm for the target than the target variant. In some embodiments, the blocker oligonucleotide is not fully complementary to either the target or target variant sequences. In some embodiments, the blocker oligonucleotide forms at least one or more mismatch with the target variant, but nevertheless, hybridizes at a sufficiently high Tm to impair a polymerase from replicating the variant sequence in the presence of the blocker oligonucleotide, while not significantly impairing replication of the target sequence. In some embodiments, the blocker oligonucleotide either has a larger number of mismatches with the target sequence than with the target variant or has different mismatches with the target sequence compared to with the target variant such that replication of the target variant sequence in the presence of the blocker oligonucleotide is impaired while replication of the target sequence in the presence of the blocker oligonucleotide is not significantly impaired. In some embodiments, the mismatch between the target and variant sequence does not occur at either the 5' or the 3' ends of the sequences. In some embodiments, the blocker oligonucleotide is designed such that the one or more mismatches are formed in the middle (not at the ends) of the hybridizing region formed by the duplex of the blocker oligonucleotide and the target variant. In some embodiments, the blocker oligonucleotide is designed such that the one or more mismatches are formed at one or both ends of the hybridizing region formed by the duplex of the blocker oligonucleotide and the target variant.

As discussed above, the Tm of the blocker oligonucleotide and a particular target variant is sufficiently higher than the Tm of the blocker oligonucleotide for the target sequences such that replication of the target variant is impaired whereas replication of the target under the same conditions is not significantly impaired, thereby allowing for detection of the target sequence in the presence of the target variant. In some embodiments, the difference in Tm of the blocker oligonucleotide for the target variant compared to for the target sequence is at least about 5° C., 10° C., 15° C., 20, or more. It will be appreciated that the Tm can be measured in different ways. The $T_m$ can be determined using any amplification buffer of other mixture that is, or emulates, the conditions at which replication with the polymerase is tested. One example of such conditions is, e.g., 2.5% glycerol, 50 mM Tricine pH 8.3, 45 mM potassium acetate with appropriate nucleotides for primer extension.

The blocker oligonucleotides of the invention can be of any length. In some embodiments, blocker oligonucleotides are between 5-200 nucleotides, e.g., 5-100, 10-100, 5-40, 5-25, 10-50, 15-50, nucleotides long.

In some embodiments, the blocker oligonucleotides of the invention comprise, and sometimes only include, naturally-occurring nucleotides (i.e., A, C, T, G, and U). Alternatively, in some embodiments, the blocker oligonucleotides comprises at least one (e.g., 1, 2, 3, 4, 5, 6, etc.) artificial (i.e., other than those that occur in naturally-occurring RNA or DNA) nucleotide. Exemplary artificial bases that contribute to increased $T_m$ are described in the art, including but not limited to, e.g., Lebedev et al., *Geneteic Analysis—Biomolecular Engineering* 13:15-21 (1996); Xodo, et al., *Nucleic Acids Res.* 19:5625-5631 (1991); Froehler, et al., *Tetrahedron Lett.* 33:5307-5310 (1992); Kutyavin, et al., *Biochemistry* 35:11170-11176 (1996); Nguyen, et al., *Nucleic Acids Res.* 25:30599-65 (1997). For example, 2-Amino A increases Tm by about 3° C. over A, 5-Methyl-C raises the Tm about 1.3° C. over C, C-5 propynyl-C improves the Tm about 2.8° C. over C and C-5 propynyl-U increases the Tm about 1.7° C. over T. In some embodiments, the blocker oligonucleotide of the invention does not comprise any intercalating nucleotides. In some embodiments, the blocker oligonucleotide of the invention does not comprise an internal intercalating pseudonucleotide, such as those described in WO 2006/026828.

In some embodiments, the blocker oligonucleotides of the invention comprise at least one non-nucleotide moiety (optionally, other than an intercalating nucleotide) that increases the melting temperature of the blocker oligonucleotide. Examples of such non-nucleotide moieties include, e.g., minor group binders. See, e.g., U.S. Pat. No. 6,486,308.

In some embodiments of the invention, the blocker oligonucleotide is detectably labeled and thus is of further use in detecting the target sequence in a mixture. In some embodiments, for example, the detectably labeled blocker oligonucleotide is used to detect and quantify the target sequence in an amplification reaction, including but not limited to a real-time amplification reaction. A wide variety of detectable labels are known. Exemplary labels include fluorescent labels (including, e.g., quenchers or absorbers), non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase), and the like. Labels may provide signals detectable by fluorescence, radioactivity, colorimetry, gravimetry, X-ray diffraction or absorption, magnetism, enzymatic activity, and the like. Labels can be used to provide a detectable (and optionally quantifiable) signal, and which can be attached to a nucleic acid or protein.

In certain embodiments of the invention, a label is a fluorescent dye or fluorophore. Typically, a particular fluorophore can emit light of a particular wavelength following absorbance of light of shorter wavelength. The wavelength of the light emitted by a particular fluorophore is characteristic of that fluorophore. Thus, a particular fluorophore can be detected by detecting light of an appropriate wavelength following excitation of the fluorophore with light of shorter wavelength. Fluorescent labels may include dyes that are negatively charged, such as dyes of the fluorescein family, or dyes that are neutral in charge, such as dyes of the carboxyrhodamine family, or dyes that are positively charged, such as dyes of the cyanine family or the rhodamine family. Other families of dyes that can be used in the invention include, e.g., polyhalofluorescein-family dyes, hexachlorofluorescein-family dyes, coumarin-family dyes, oxazine-family dyes, thiazine-family dyes, squaraine-family dyes, chelated lanthanide-family dyes, ALEXA FLUOR® dyes, and BODIPY®-family dyes. Dyes of the fluorescein family include, e.g., FAM, HEX, TET, JOE, NAN and ZOE. Dyes of the carboxyrhodamine family include Texas Red, ROX, R110, R6G, and TAMRA. FAM, HEX, TET, JOE, NAN, ZOE, ROX, R110, R6G, and TAMRA are marketed by Perkin-Elmer (Foster City, Calif.), while Texas Red is marketed by Molecular Probes, Inc. (Eugene, Oreg.). Dyes of the cyanine family include Cy2, Cy3, Cy3.5, Cy5, Cy5.5, and Cy7 and are marketed by Amersham GE Healthcare (Piscataway, N.J.).

IV. Polymerases with Impaired 5'-3' Nuclease Activity

A number of polymerases significantly lacking 5'-3' nuclease activity are known in the art. The N-terminal region of polymerases typically confer 5'-3' nuclease activity. Thus, mutation or deletion of all or part of the N-terminus of a polymerase can be used to generate polymerases that significantly lack 5'-3' nuclease activity. Exemplary polymerases that significantly lack 5'-3' nuclease activity include the Klenow fragment of *E. coli* DNA polymerase I; a *Thermus aquaticus* Taq lacking the N-terminal 235 amino acids (e.g., as described in U.S. Pat. No. 5,616,494); and/or a thermostable DNA polymerase having sufficient deletions (e.g., N-terminal deletions), mutations, or modifications so as to eliminate or inactivate the domain responsible for 5' to 3' nuclease activity. See, e.g., U.S. Pat. No. 5,795,762. Such polymerases are generally isolated or purified polymerases and can be recombinant proteins.

Polymerases that function in amplification reactions, including thermocycling amplification reactions are particularly useful in the invention. Polymerases useful for the methods of the invention lack significant 5'-3' nuclease activity such that the polymerase is unable to extend a primer in a template-dependent manner through the region of a target variant template at which the blocker oligonucleotide hybridizes, but is able to extend a primer through a region of a target template at which the blocker oligonucleotide hybridizes, wherein the $T_m$ of the blocker oligonucleotide is higher for the target variant template than the $T_m$ for the target template. Thus, those of skill in the art will appreciate that the precise level, if any, of 5'-3' nuclease activity in the polymerase can vary depending on $T_m$ of the blocker oligonucleotide for the target and target variant.

According to the methods of the invention, the polymerase significantly lacking 5'-3' nuclease activity is sufficiently impaired by the blocker oligonucleotide from replicating the target variant sequence to the benefit of a corresponding amplification of the target. Without intending to limit the scope of the present invention, it is believed that there can be a competition reaction between a target sequence and a closely related target variant. In situations where there is considerably more copies of the target variant compared to the target, amplification in the absence of the blocker results in amplification such that the target sequence has reduced detectability or is not detectable. When it is desirable to detect the target in the presence of the target variant, the amplification of the variant is impaired by hybridization of the blocker oligonucleotide, whereas amplification of the target is not impaired or is impaired to a lesser degree to allow for detection of the target in the presence of the target variant. The amplification of the target variant is considered to be significantly impaired when the presence of the blocker oligonucleotide reduces the amount of variant amplicon by at least 20%, and more typically at least 50%, 75%, 90%, 95% or more, compared to a control reaction lacking the blocker oligonucleotide.

In some embodiments, a control reaction is also performed employing a polymerase having significant 5'-3' nuclease activity instead of a polymerase significantly lacking 5'-3' nuclease activity. Such control reactions can be useful for determining the presence or absence of target variants as in such control reactions the target variants are amplified. Such control reactions can also be useful in confirming that the amplification reagents are functional. It will be appreciated that other, different controls can also be used.

V. Uses of the Methods

The present invention is useful for detecting target sequences and nucleic acids comprising target sequences. The invention is particularly useful for detecting a target sequence in the presence or target variants, especially where the target variants are in excess concentration compared to the target sequence to be detected. Without intending to limit the scope of the invention, some examples of such situations are detection of somatic mutations or mutations related to cancer. For example, the present invention is useful for detection of cancer or other somatic mutations in a biopsy where most of the cells likely have a "normal" version of a gene sequence (i.e., the target variant), but at least a few cells may have a mutation, (i.e., the target sequence).

The present invention can be used to analyze and detect nucleic acids in any sample, including biological samples as defined herein. Samples used in the methods of the invention can have both target and target variant sequences, only target or target variant sequences or neither. In some embodiments, the presence of a target or target variant is known, whereas in other embodiments, it is not known whether a target or target variant is present.

VI. Reaction Mixtures

The present invention also provides reaction mixtures involved in the methods of the invention. Any reaction mixtures as described above can be generated. An exemplary reaction mixture comprises, for example, a polymerase significantly lacking 5'-3' nuclease activity; a polynucleotide comprising a target sequence; a polynucleotide comprising a second sequence, wherein the second sequence differs from the target sequence by at least one nucleotide; and a blocker oligonucleotide, wherein the blocker oligonucleotide hybridizes to the second sequence sufficiently to impair amplification of the second sequence by the polymerase, but hybridization of the oligonucleotide to the target sequence does not significantly impair amplification of the target sequence. In some embodiments, the reaction mixtures comprises nucleotides (e.g., dNTPs such as dATP, dCTP, dGTP, dTTP, and/or dUTP, or in any combination thereof) at concentrations useful for primer extension and/or amplification reactions. In some embodiments, the reaction mixtures comprise one or more different primers that hybridize to the target and/or second sequence, e.g., at least one primer that hybridizes upstream of the region where the blocker oligonucleotide hybridizes and/or a primer pair comprising the 5' sense primer and a corresponding 3' antisense primer. In other, non-mutually exclusive variations, the reaction mixture includes one or more containers providing free nucleotides (conventional and/or unconventional). In some embodiments, the reaction mixture includes alpha-phosphorothioate dNTPs, dUTP, dITP, and/or labeled dNTPs such as, e.g., fluorescein- or cyanin-dye family dNTPs. The specific blocker oligonucleotide, polymerase, primers, and other reagents described herein can also be included in the reaction mixtures as detailed in the above sections. In some embodiments, the kit further includes a container providing a 5' sense primer hybridizable, under primer extension conditions, to the target and/or second sequence.

VII. Kits

The present invention also provides kits for use in the methods of the invention. Typically, the kit is compartmentalized for ease of use and contains at least one container providing a polymerase significantly lacking 5'-3' nuclease activity. One or more additional containers providing additional reagent(s) can also be included. Such additional containers can include any reagents or other elements recognized by the skilled artisan for use in primer extension procedures in accordance with the methods described above, including reagents for use in, e.g., nucleic acid amplification procedures (e.g., PCR, RT-PCR), DNA sequencing procedures, or DNA labeling procedures. The kit can comprise, for example, a polynucleotide comprising a target sequence; a polynucleotide comprising a second sequence, wherein the second sequence differs from the target sequence by at least one nucleotide; and a blocker oligonucleotide, as described herein. In some embodiments, the kit further includes a container providing a 5' sense primer hybridizable, under primer extension conditions, to the target and/or second sequence, and/or a primer pair comprising the 5' sense primer and a corresponding 3' antisense primer. In other, non-mutually exclusive variations, the kit includes one or more containers providing free nucleotides (conventional and/or unconventional). In specific embodiments, the kit includes alpha-phosphorothioate dNTPs, dUTP, dITP, and/or labeled dNTPs such as, e.g., fluorescein- or cyanin-dye family dNTPs. In still other, non-mutually exclusive embodiments, the kit includes one or more containers providing a buffer suitable for a primer extension reaction.

EXAMPLES

The following examples are offered to illustrate, but not to limit the claimed invention.

Example 1

This example illustrates use of a blocker oligonucleotide to suppress amplification of a Factor 5 wild type allele using melt curve analysis to detect the mutant allele.

In the current example, the asymmetric PCR sample master mix consisted of: 2.5% glycerol; 50 mM Tricine, pH 8.3; 45 mM potassium acetate; 200 uM DATP, 200 uM dGTP, 200 uM dCTP, 400 uM dUTP; 0.7 uM upstream (excess) primer; 0.1 µM downstream (limiting) primer; 0.4 µM detection probe; 4U uracil-N-glycosylase; 40 U AZO5 DNA polymerase or ZO5 DNA polymerase; and 4 mM magnesium acetate.

The master mix was used to amplify Factor 5 wild type and mutant plasmid DNA targets. The excess primer was present at 7× the limiting primer concentration to ensure an excess of single-stranded amplicon for the detection probe to bind to. The amplification and melting were performed on the Roche Lightcycler LC480.

The thermal cycling profile used for the example was: 50° C. for 5 minutes (UNG step); 94° C. for 15 seconds-59° C. for 40 seconds×2 cycles; 91° C. for 15 seconds-59° C. for 40 seconds×48 cycles, 94° C. for 30 seconds, with data collection during the 59° C. annealing step; and a melting step with constant data collection between 40° C. to 950.

Figure 2:
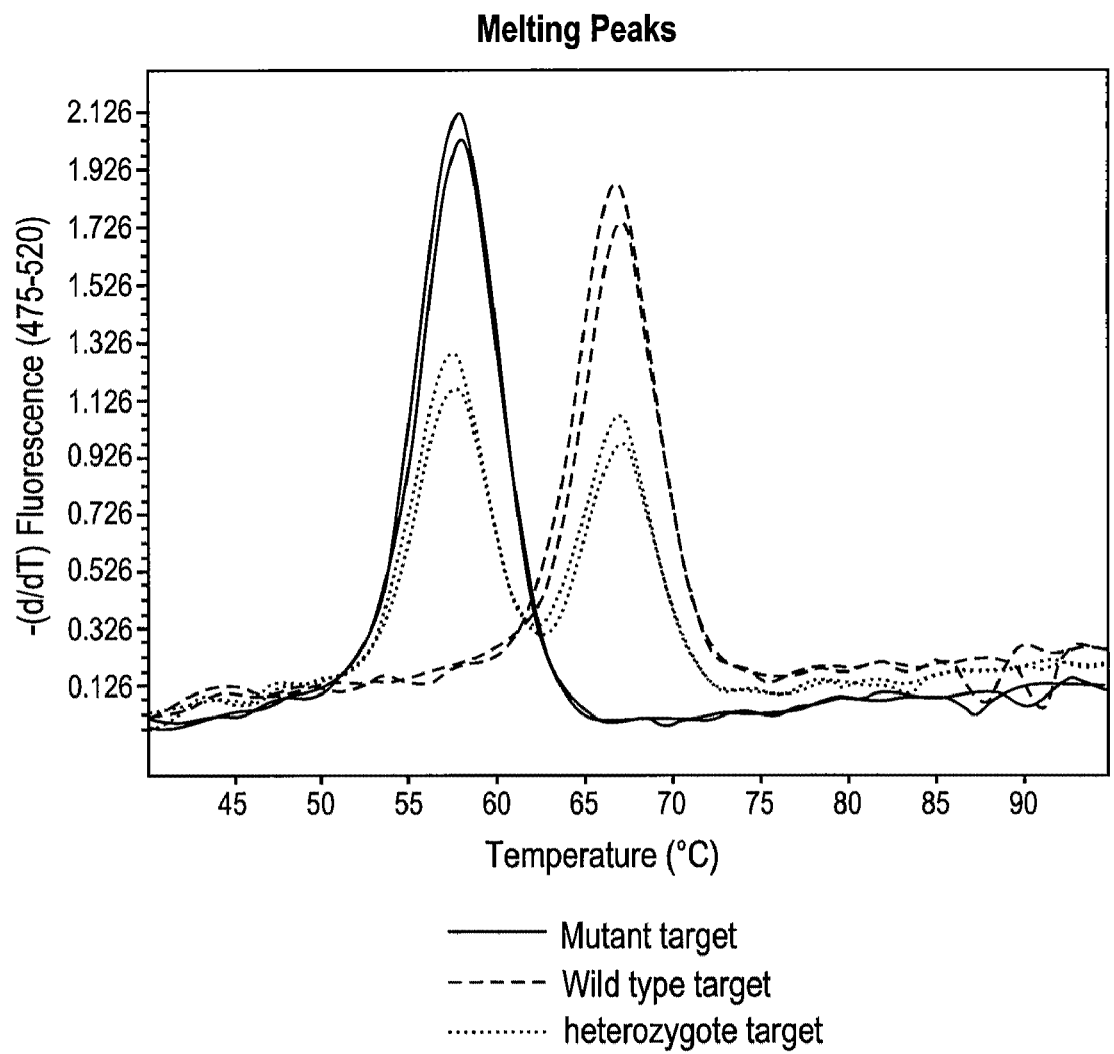
FIG. 2 illustrates melting data from ZO5 DNA polymerase amplification of Factor 5 wildtype and mutant DNA in the presence of an unstabilized detection probe that is fully complementary to the wildtype sequence and has one mismatch with the mutant sequence, as detailed in the Examples.
Figure 3:
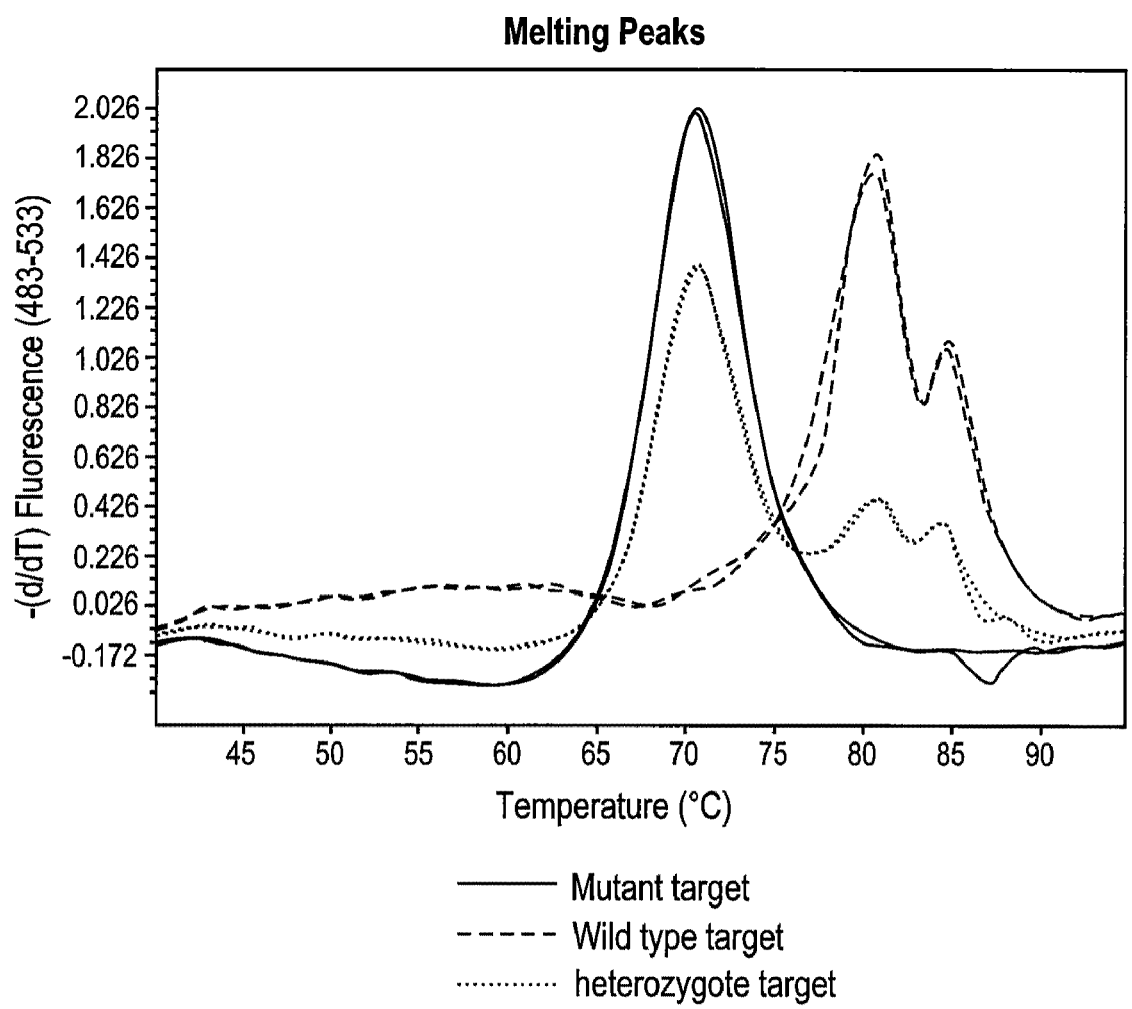
FIG. 3 illustrates melting data from ZO5 DNA polymerase amplification of Factor wildtype and mutant DNA in the presence of a stabilized detection probe (blocker) that is fully complementary to the wildtype sequence and has one mismatch with the mutant sequence, as detailed in the Examples.

The sequence of the upstream primer was TGAACCCA-CAGAAAATGATGCCCE (SEQ ID NO: 1); the sequence of the downstream primer was GGAAATGCCCCATTATT-TAGCCAGGBz (SEQ ID NO:2); Bz=t-butyl benzyl dA. The sequence of the stabilized detection probe (blocker) was EFFLLFLGLLFGFLLAGGGQ (SEQ ID NO:3), where E=cx-FA$\overline{M}$, Q=BHQ2, F=propynyl dU, and L=propynyl dC, and P=3' phosphate. The sequence of a unstabilized detection probe (non-blocker) was ECTGTATTCCT CGCCTGTCCAGQP (SEQ ID NO:4), where E=cx-FAM, $\overline{Q}$=BHQ2, F=propynyl dU, L=propynyl dC, and P=3' phosphate. These oligonucleotides are perfectly matched to the wild type target, and have one mismatch to the mutant target (CA mismatch), indicated in bold and underlined The melting data from this example showed that with ZO5 DNA polymerase, both probes gave melting curves as expected, with the wild type giving the highest Tm, the mutant target giving the lowest $T_m$ and the heterozygote giving Tms for both the wild type and mutant alleles (FIG. 2 & FIG. 3). Because ZO5 cleaved the probe, no suppression of amplification was observed. It can be seen that the Tm of the stabilized probe to the 2 alleles was approximately 12° C. higher than the unstabilized probe. Also, an unidentified higher Tm peak was also observed, as a shoulder on the right side of the main melting peak.

Figure 4:
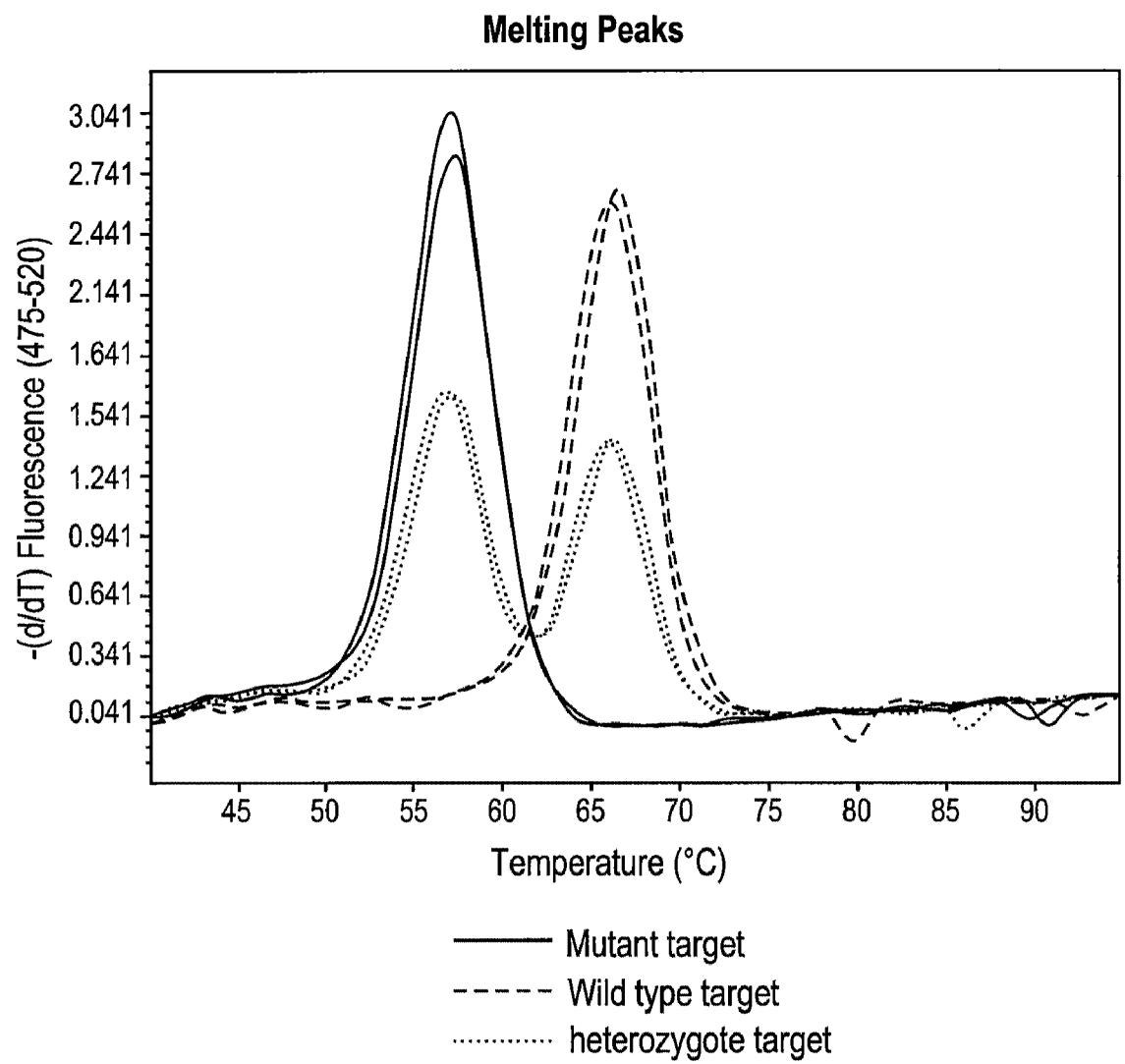
FIG. 4 illustrates melting data from ΔZO5 DNA polymerase (a polymerase lacking 5'-3' nuclease activity—see, e.g., U.S. Pat. No. 5,466,591) amplification of Factor 5 wildtype and mutant DNA in the presence of an unstabilized detection probe that is fully complementary to the wildtype sequence and has one mismatch with the mutant sequence, as detailed in the Examples.

With ΔZO5, the unstabilized probe again gave the same melting curves, but with more signal as the probe was not degraded during PCR (FIG. 4).

Figure 5:
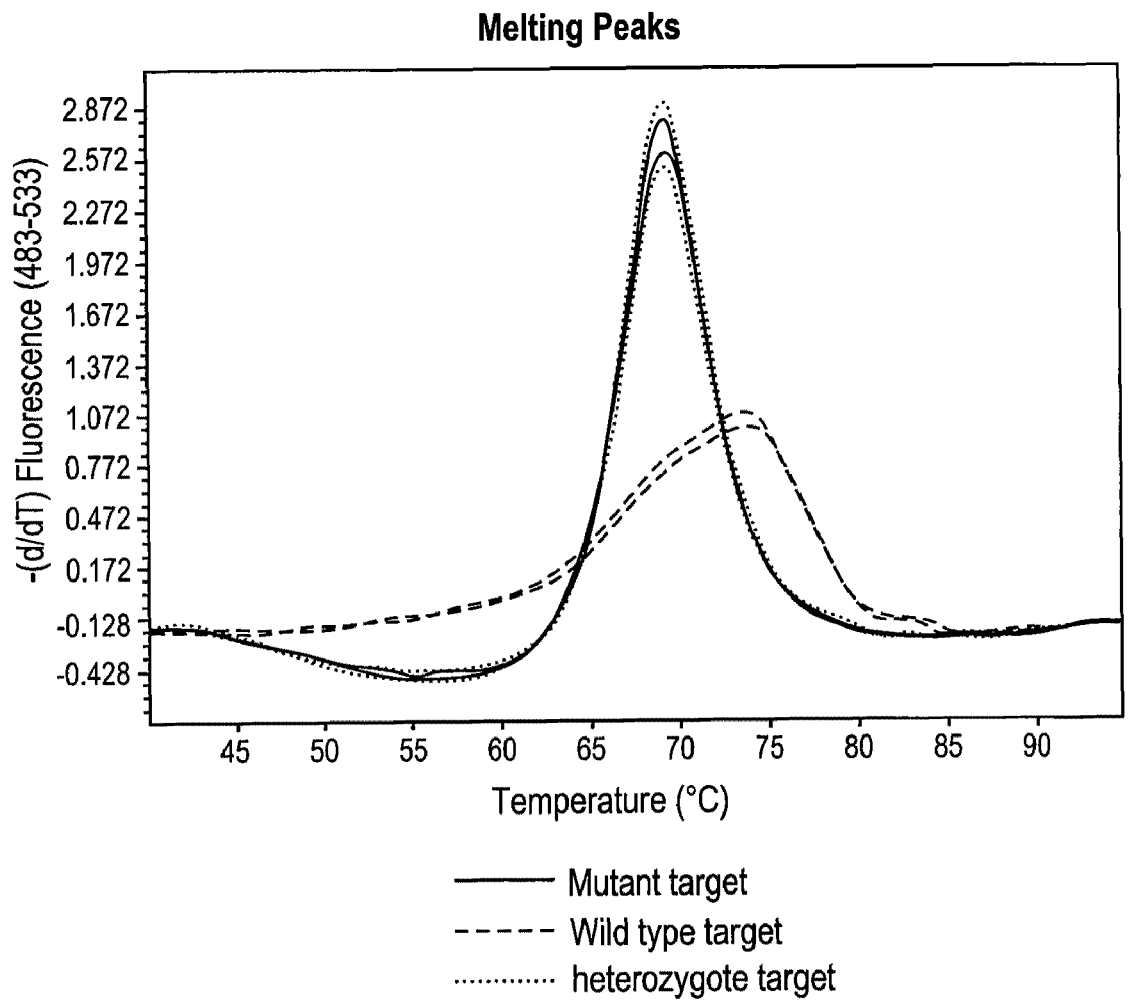
FIG. 5 illustrates melting data from ΔZO5 DNA polymerase (lacking 5'-3' nuclease activity) amplification of Factor 5 wildtype and mutant DNA in the presence of a stabilized detection probe (blocker) that is fully complementary to the wildtype sequence and has one mismatch with the mutant sequence, as detailed in the Examples.

When ΔZO5 was used with the stabilized probe however (FIG. 5), the wild type allele in the heterozygote sample did not result in a melt curve for the wild type allele; a melt curve that was identical to the mutant target resulted, indicating that amplification of the wild type allele had been suppressed. The pure wild type target resulted in a melting curve that was much lower and broader than the wild type target with ZO5 (FIG. 3).

Example 2

Figure 6:
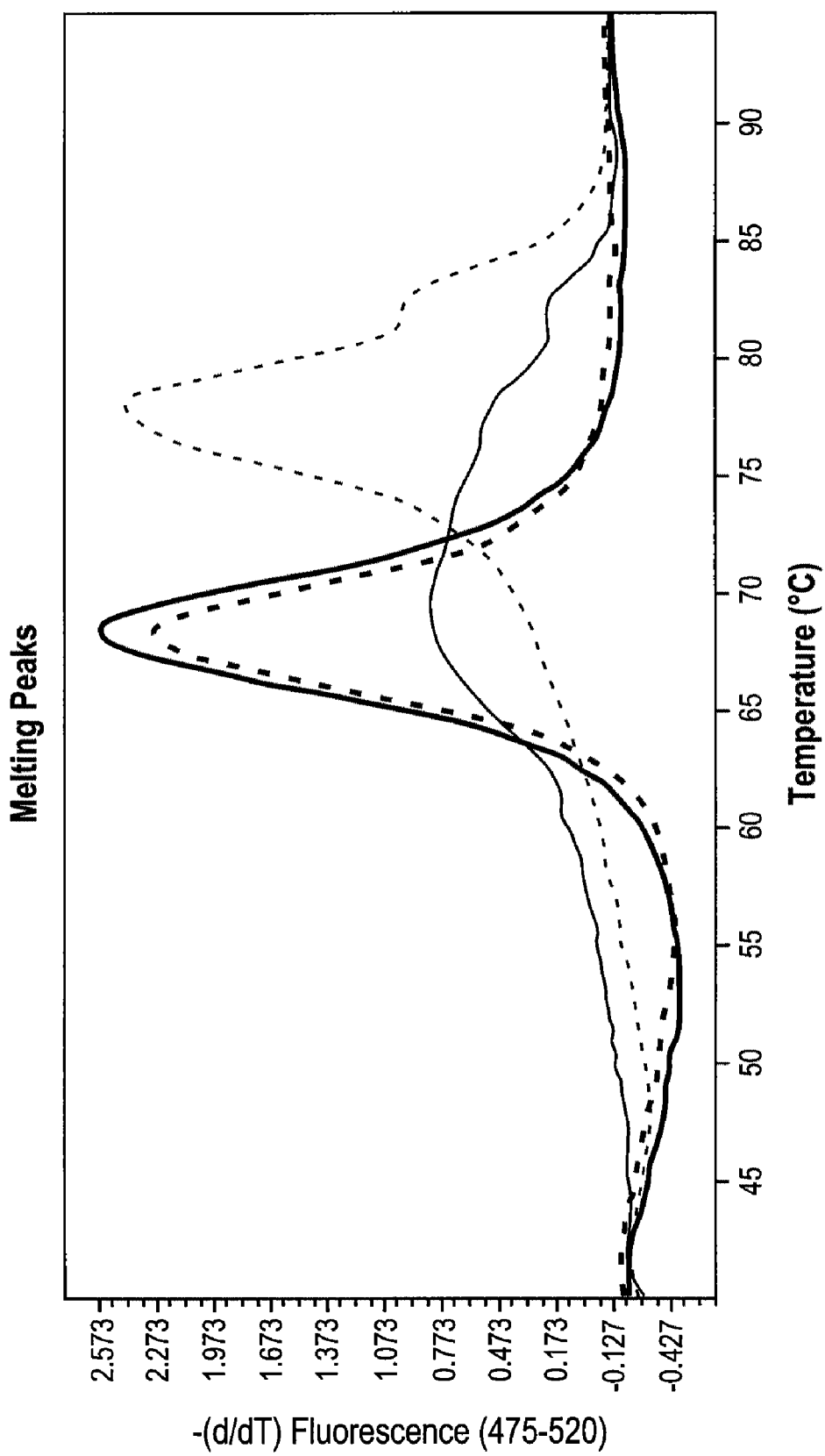
FIG. 6 illustrates melting data from ΔZO5 DNA polymerase (lacking the 5'-3' nuclease domain) amplification of Factor 5 wildtype and mutant DNA in the presence or absence of a stabilized detection probe (blocker) that is fully complementary to the wildtype sequence and has one mismatch with the mutant sequence, as detailed in the Examples. In this figure, the blocker was either present in the PCR tube from the beginning, or was added post-PCR. When the probe was not present during PCR, normal amplification of both wild type (dark dotted line) and mutant (light dotted line) targets occurred. When the probe was present during PCR, the mutant target (dark solid line) still amplified and melted well, but the wild type (light solid line) did not.

Further evidence of the effect on amplification using a stable probe and a non-cleaving enzyme is shown in FIG. 6. Using the same amplification conditions described in example 1 with AZO5, a stabilized probe was either present in the PCR tube from the beginning, or was added post-PCR. A melt was then performed, and the data is shown in FIG. 6.

When the probe was not present during PCR, normal amplification of both wild type (dark dotted line) and mutant (light dotted line) targets occurred. When the probe was present during PCR, the mutant target (dark solid line) still amplified and melted well, but the wild type (light solid line) did not.

Example 3

Suppression was also observed in real-time PCR. Using the same PCR conditions described in Example 1, growth curve data from the same experiment showed a threshold cycle (Ct) delay of about 12 cycles between the wild type and mutant targets using AZO5, compared to no delay with Z05. In addition, to test whether the blocking oligonucleotide works because of the stabilizing bases present (propynyl dU & propynyl dC), a long unstabilized probe (52-mer) was made and tested, that had the same $T_m$ as the short stabilized probe. The sequence of this probe was: ECAAGGACAAAATACCT-GTQATTCCT CGCCTGTCCAGGGATCTGCTCTTACAGP (SEQ ID NO:5 and 6, where E=cx-FAM, Q=BHQ2, and P=3' phosphate). A 11 cycle delay was observed between the wild type and mutant targets using ΔZO5, compared to no delay using ZO5. This result indicated that Tm was the most critical factor in determining whether a probe can act as a blocker.

Example 4

An experiment was performed to mimic a rare mutation detection assay. Using the reaction conditions described in example 1, wild type and mutant plasmid DNA targets were mixed together in different ratios to see what level of mutant targets can be detected in a background of wild type targets. Ratios of 100:1 (corresponding to 10,000 copies wild type+ 100 copies of mutant), 500:1 (50,000 copies wild type+100 copies of mutant), 1000:1 (100,000 copies wild type+100 copies of mutant), 5000:1 (500,000 copies wild type+100 copies of mutant) and 10,000:1 (1,000,000 copies wild type+ 100 copies of mutant) were prepared. Clear interpretable melt curves were observed for the mutant target up to a ratio of 1000:1. Above this, the melt curve from the wild type started to interfere with the mutant melt curve, indicating that efficient blocking of amplification of the wild type target was no longer occurring.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of detecting a target sequence in a polynucleotide in a biological sample, wherein the sample also contains a second polynucleotide comprising a second sequence, wherein the second sequence differs from the target sequence by at least one nucleotide, the method comprising, i. contacting the sample with a blocker oligonucleotide under conditions to allow for hybridization of the blocker oligonucleotide to the second sequence or the target sequence, wherein the blocker oligonucleotide comprises a non-natural nucleotide that results in a higher melting temperature of the blocker oligonucleotide compared to insertion of a naturally-occurring nucleotide in the non-natural nucleotide's position;

ii. contacting the sample in the presence of the hybridized blocker oligonucleotide with at least one primer and a polymerase significantly lacking 5'-3' nuclease activity under conditions such that template-dependent extension of the primer occurs, wherein the primer hybridizes to the polynucleotides, upstream of the blocker oligonucleotide-hybridizing sequence;

wherein the blocker oligonucleotide hybridizes to the second sequence sufficiently to impair amplification of the second sequence by the polymerase, wherein the blocker oligonucleotide does not comprise an intercalating nucleotide, and further wherein hybridization of the oligonucleotide to the target sequence does not significantly impair amplification of the target sequence by the polymerase significantly lacking 5'-3' nuclease activity, wherein the blocker oligonucleotide hybridized to the second sequence would not block a polymerase having 5'-3' nuclease activity.

2. The method of claim 1, wherein the target sequence is between 5-100 nucleotides long.

3. The method of claim 1, wherein the sample comprises the target sequence and the second sequence.

4. The method of claim 3, wherein the second sequence are present in the sample at a concentration at least ten-fold higher than the concentration of target sequence.

5. The method of claim 1, wherein the blocker oligonucleotide is detectably-labeled.

6. The method of claim 1, wherein there is a single nucleotide difference between the second and target sequences and the blocker oligonucleotide is fully complementary to the target sequence except for at the position of the single nucleotide.

7. The method of claim 1, wherein there are 2-6 nucleotide differences between the second and target sequences and the blocker oligonucleotide is fully complementary to the target sequence except for at the positions of the 2-6 nucleotides.

8. The method of claim 1, wherein the difference between:
the melting temperature of the blocker oligonucleotide and the second sequence; and
the melting temperature of the blocker oligonucleotide and the target sequence is at least 5° C. as measured in 2.5% glycerol, 50 mM Tricine pH 8.3, 45 mM potassium acetate.

9. The method of claim 1, wherein the blocker oligonucleotide comprises at least one non-natural nucleotide, wherein the non-natural, non-intercalating nucleotide increases the melting temperature of the blocker oligonucleotide compared to a control oligonucleotide that is otherwise identical to the blocker oligonucleotide except that has a natural nucleotide in the place of the non-natural nucleotide.

10. The method of claim 1, wherein the blocker oligonucleotide comprises at least one non-nucleotide moiety, wherein the non-nucleotide moiety increases the melting temperature of the blocker oligonucleotide compared to a control oligonucleotide that is otherwise identical to the blocker oligonucleotide except that lacks the non-nucleotide moiety.

11. The method of claim 10, wherein the non-nucleotide moiety binds a minor groove of DNA.

12. The method of claim 1, wherein the blocker oligonucleotide hybridizes to the second sequence with a melting temperature of at least 70° C. as measured in 2.5% glycerol, 50 mM Tricine pH 8.3, 45 mM potassium acetate.

13. The method of claim 1, wherein the blocker oligonucleotide, if comprising only natural nucleotides and hybridized to the second sequence, would not block a polymerase having 5'-3' nuclease activity.

* * * * *

UNITED STATES PATENT AND TRADEMARK OFFICE
CERTIFICATE OF CORRECTION

| | |
|---|---|
| PATENT NO. | : 8,071,338 B2 |
| APPLICATION NO. | : 12/186311 |
| DATED | : December 6, 2011 |
| INVENTOR(S) | : Nicolas Newton |

Page 1 of 1

It is certified that error appears in the above-identified patent and that said Letters Patent is hereby corrected as shown below:

In the Claims:

In column 26, claim 9, line 17, please delete "that".

In column 26, claim 10, line 24, please delete "that".

Signed and Sealed this
Eleventh Day of March, 2014

Michelle K. Lee
*Deputy Director of the United States Patent and Trademark Office*

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:Factor 5
      wild type allele asymmetric PCR amplification upstream primer
<220> FEATURE:
<221> NAME/KEY: modified_base
<222> LOCATION: (24)
```

```
<223> OTHER INFORMATION: n = t-butyl benzyl dA

<400> SEQUENCE: 1
tgaacccaca gaaaatgatg cccn                                          24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence:Factor 5
      wild type allele asymmetric PCR amplification downstream primer
<220> FEATURE:
<221> NAME/KEY: modified_base
<222> LOCATION: (26)
<223> OTHER INFORMATION: n = t-butyl benzyl dA

<400> SEQUENCE: 2
ggaaatgccc cattatttag ccaggn                                        26

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:Factor 5
      wild type allele asymmetric PCR amplification stabilized
      detection probe (blocker)
<220> FEATURE:
<221> NAME/KEY: modified_base
<222> LOCATION: (1)
<223> OTHER INFORMATION: n = propynyl dU modified by abasic
      phosphoramidite cx-FAM, where cx-FAM = cyclohexane linker bound
      to 6-carboxyfluorescein (FAM)
<220> FEATURE:
<221> NAME/KEY: modified_base
<222> LOCATION: (2)
<223> OTHER INFORMATION: n = propynyl dU
<220> FEATURE:
<221> NAME/KEY: modified_base
<222> LOCATION: (3)..(4)
<223> OTHER INFORMATION: n = propynyl dC
<220> FEATURE:
<221> NAME/KEY: modified_base
<222> LOCATION: (5)
<223> OTHER INFORMATION: n = propynyl dU
<220> FEATURE:
<221> NAME/KEY: modified_base
<222> LOCATION: (6)
<223> OTHER INFORMATION: n = propynyl dC
<220> FEATURE:
<221> NAME/KEY: modified_base
<222> LOCATION: (8)..(9)
<223> OTHER INFORMATION: n = propynyl dC
<220> FEATURE:
<221> NAME/KEY: modified_base
<222> LOCATION: (10)
<223> OTHER INFORMATION: n = propynyl dU
<220> FEATURE:
<221> NAME/KEY: modified_base
<222> LOCATION: (12)
<223> OTHER INFORMATION: n = propynyl dU
<220> FEATURE:
<221> NAME/KEY: modified_base
<222> LOCATION: (13)..(14)
<223> OTHER INFORMATION: n = propynyl dC
<220> FEATURE:
<221> NAME/KEY: modified_base
<222> LOCATION: (18)
<223> OTHER INFORMATION: g modified by Black Hole Quencher BHQ2 (Q)

<400> SEQUENCE: 3
nnnnnngnnn gnnnaggg                                                 18
```

```
<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:Factor 5
      wild type allele asymmetric PCR amplification unstabilized
      detection probe (non-blocker)
<220> FEATURE:
<221> NAME/KEY: modified_base
<222> LOCATION: (1)
<223> OTHER INFORMATION: c modified by 5' abasic phosphoramidite
      cx-FAM, where cx-FAM = cyclohexane linker bound to
      6-carboxyfluorescein (FAM)
<220> FEATURE:
<221> NAME/KEY: modified_base
<222> LOCATION: (21)
<223> OTHER INFORMATION: g modified by Black Hole Quencher BHQ2 (Q)
      and 3' phosphate (P)

<400> SEQUENCE: 4
ctgtattcct cgcctgtcca g                                           21

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:Factor 5
      wild type allele real-time PCR long unstabilized probe
<220> FEATURE:
<221> NAME/KEY: modified_base
<222> LOCATION: (1)
<223> OTHER INFORMATION: c modified by abasic phosphoramidite
      conjugated to cx-FAM, where cx-FAM = cyclohexane linker bound to
      6-carboxyfluorescein (FAM)
<220> FEATURE:
<221> NAME/KEY: modified_base
<222> LOCATION: (18)
<223> OTHER INFORMATION: t modified by abasic phosphoramidite
      conjugated to Black Hole Quencher BHQ2 (Q) in sugar-phosphate
      backbone attached to 5' end of SEQ ID NO:6

<400> SEQUENCE: 5
caaggacaaa atacctgt                                               18

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence:Factor 5
      wild type allele real-time PCR long unstabilized probe
<220> FEATURE:
<221> NAME/KEY: modified_base
<222> LOCATION: (1)
<223> OTHER INFORMATION: a modified by abasic phosphoramidite
      conjugated to Black Hole Quencher BHQ2 (Q) in sugar-phosphate
      backbone attached to 3' end of SEQ ID NO:5
<220> FEATURE:
<221> NAME/KEY: modified_base
<222> LOCATION: (33)
<223> OTHER INFORMATION: g modified by 3' phosphate

<400> SEQUENCE: 6
attcctcgcc tgtccaggga tctgctctta cag                              33
```